(12) United States Patent
Ahn et al.

(10) Patent No.: US 10,219,779 B2
(45) Date of Patent: Mar. 5, 2019

(54) METHOD AND APPARATUS FOR GENERATING CARDIAC LEFT VENTRICULAR THREE-DIMENSIONAL IMAGE

(71) Applicant: Institute for Basic Science, Daejeon (KR)

(72) Inventors: Chi Young Ahn, Daejeon (KR); Ki Wan Jeon, Daejeon (KR); Sang Woon Yun, Seoul (KR)

(73) Assignee: Institute for Basic Science, Daejeon (KR)

( * ) Notice: Subject to any disclaimer, the term of this patent is extended or adjusted under 35 U.S.C. 154(b) by 250 days.

(21) Appl. No.: 14/741,155

(22) Filed: Jun. 16, 2015

(65) Prior Publication Data
US 2015/0366533 A1 Dec. 24, 2015

(30) Foreign Application Priority Data

Jun. 18, 2014 (KR) .................. 10-2014-0074623

(51) Int. Cl.
*A61B 8/08* (2006.01)
*G06T 7/00* (2017.01)
*A61B 8/00* (2006.01)

(52) U.S. Cl.
CPC ............ *A61B 8/0883* (2013.01); *A61B 8/466* (2013.01); *A61B 8/5223* (2013.01); *G06T 7/0012* (2013.01); *G06T 2207/30048* (2013.01)

(58) Field of Classification Search
CPC .......... A61B 8/00; G06T 2207/00; G06T 7/00
See application file for complete search history.

(56) References Cited

U.S. PATENT DOCUMENTS 6,106,466 A * 8/2000 Sheehan ............ A61B 5/1075
128/916
6,873,718 B2 * 3/2005 O'Donnell ............ G06T 7/0012
382/131

(Continued)

FOREIGN PATENT DOCUMENTS

KR 10-1998-0042140 U 9/1998
WO WO 93/15659 A1 8/1993

OTHER PUBLICATIONS

Coppini, Giuseppe, Riccardo Poli, and Guido Valli. "Recovery of the 3-D shape of the left ventricle from echocardiographic images." IEEE transactions on medical imaging 14.2 (1995): 301-317.*

(Continued)

*Primary Examiner* — Luther G Behringer
*Assistant Examiner* — Sean D Mattson
(74) *Attorney, Agent, or Firm* — Wolf, Greenfield & Sacks, P.C.

(57) ABSTRACT

An apparatus for generating a 3D left ventricle image includes: an ultrasonic sensor transmitting ultrasonic waves to the heart and receiving echoes thereof, an image processor acquiring a plurality of 2D left ventricle images based on the echoes of the ultrasonic waves and extracting sets of left ventricle boundary coordinates from the plurality of 2D images, respectively and a controller calculating a position of the left ventricle in 3D space through transformation of the sets of left ventricle boundary coordinates extracted by the image processor and generating a 3D left ventricle image based on the position of the left ventricle in 3D space.

6 Claims, 3 Drawing Sheets

(56) References Cited

U.S. PATENT DOCUMENTS

| | | | |
|---|---|---|---|
| 2005/0197696 A1* | 9/2005 | Gomez Duran | A61F 2/2448 623/2.37 |
| 2009/0074280 A1* | 3/2009 | Lu | A61B 8/00 382/131 |
| 2010/0280384 A1 | 11/2010 | Song et al. | |
| 2012/0002840 A1* | 1/2012 | Linnenbank | G06K 9/32 382/103 |
| 2012/0041313 A1 | 2/2012 | Tanaka et al. | |
| 2016/0249885 A1* | 9/2016 | Schneider | A61B 8/0883 382/131 |

OTHER PUBLICATIONS

Csiszár, Imre. "Information geometry and alternating minimization procedures." Statistics and decisions 1 (1984): 205-237.*

Janz, Ronald F., and Arthur F. Grimm. "Finite-Element Model for the Mechanical Behavior of the Left Ventricle: prediction of deformation in the potassium-arrested rat heart." Circulation research 30.2 (1972): 244-252.*

Bathe, Mark, and R. D. Kamm. "A fluid-structure interaction finite element analysis of pulsatile blood flow through a compliant stenotic artery." Journal of Biomechanical Engineering 121.4 (1999): 361-369.*

Bänsch et al., Riccati-Based Boundary Feedback Stabilization of Incompressible Navier-Stokes Flow. Deutschet Forschungsgemeinschaft Preprint-No. SPP1253-154; Sep. 2013; p. 1-28.

Hendabadi et al., Topology of Blood Transport in the Human Left Ventricle by Novel Processing of Doppler Echocardiography. Ann Biomed Eng. 41(12); Dec. 2013; p. 1-26.

Im, A Finite Difference Code for the Navier-Stokes Equations in Vorticity/Stream Function Formulation. University of Michigan Presentation. Fall 2001. 47 pages.

\* cited by examiner

METHOD AND APPARATUS FOR GENERATING CARDIAC LEFT VENTRICULAR THREE-DIMENSIONAL IMAGE

BACKGROUND

1. Technical Field

The present invention relates to a method and apparatus for generating a three-dimensional image of a left ventricle of the heart, and more particularly, to a method and apparatus for automatically generating a three-dimensional image of a left ventricle of the heart using two dimensional echocardiograms without a separate three-dimensional image photographing apparatus.

2. Description of the Related Art

Ultrasonic image diagnostic apparatuses are widely used in medicine to acquire information on an internal structure of a subject due to their easy mobility, noninvasive and nondestructive characteristics, and capabilities of providing images in real time.

In general, ultrasonic image diagnostic apparatuses provide two dimensional images of a subject by transmitting ultrasonic signals to the subject, receiving the ultrasonic signals reflected from the subject, followed by performing signal and image processing with respect to the reflected signals.

The heart is an organ that generates periodic electrical stimulation to cause contraction and relaxation of muscles, thereby circulating blood throughout the body, and, in particular, the left ventricle at the lower left in the heart purifies blood from the left atrium and sends it to the aorta.

In other words, blood receiving oxygen from the lung passes from the pulmonary vein into the left atrium and then heads for the underlying left ventricle when a wall of the left ventricle contracts. Particularly, the left ventricle has the thickest wall of the four cardiac chambers since the blood must be strongly pumped to be sent through arteries to the whole body.

The heart is the most important vital organ and thus normal function of the heart needs to be verified in various ways using the ultrasonic image diagnostic apparatuses as set forth above.

By way of example, there has been developed a technique of providing two dimensional color Doppler images for displaying velocity components of a blood flow in a direction of ultrasonic wave propagation by transmitting/receiving ultrasonic signals to/from fluid flowing within a subject, for example, a blood flow in blood vessels, followed by calculating Doppler frequencies.

One example of the related art is disclosed in Korean Patent Publication No. 10-1998-0042140 (published on Aug. 17, 1998 and entitled "Ultrasonic diagnostic imaging system for analysis of left ventricular function").

BRIEF SUMMARY

Quantitative information on the function of the heart is required for heart disease diagnosis. The quantitative information includes left ventricular hypertrophy, stroke volume, ejection fraction, cardiac output, and the like.

Since it is necessary to identify how the left ventricle shrinks and expands in a three-dimensional space in order to acquire the quantitative information on the function of the heart, there is a growing need for a technique for obtaining three-dimensional images of the left ventricle.

The present invention has been conceived to meet the need as described above, and is aimed at providing a method and apparatus for generating three-dimensional images of the left ventricle which can automatically generate a three-dimensional image of the left ventricle using a plurality of two dimensional echocardiograms captured from three different directions without a separate three-dimensional image photographing apparatus.

In accordance with one aspect of the present invention, a method for generating a 3D image of a left ventricle of the heart includes: acquiring, by an image processor, a 2D left ventricle image; extracting, by the image processor, left ventricle boundary coordinates from the 2D image; calculating, by a controller, a position of the left ventricle in 3D space through transformation of the extracted left ventricle boundary coordinates; and generating, by the controller, a 3D left ventricle image based on the calculated position of the left ventricle in 3D space.

The method may further include, before extracting the left ventricle boundary coordinates, transmitting, by an ultrasonic sensor, ultrasonic waves to the heart and receiving echoes thereof, wherein the image processor acquires the 2D left ventricle image based on the echoes of the ultrasonic waves.

In receiving the echoes of the ultrasonic waves, the ultrasonic sensor may transmit ultrasonic waves to the heart in three different directions and receive echoes thereof in each direction.

In acquiring the 2D left ventricle image, the image processor may acquire a plurality of 2D images, wherein the plurality of 2D images comprises a 2-chamber view, a 3-chamber view, and a 4-chamber view for an entire cardiac cycle.

In extracting the left ventricle boundary coordinates, the image processor may extract respective left ventricle boundary coordinates from the plurality of 2D images.

Calculating the position of the left ventricle in 3D space through transformation of the left ventricle boundary coordinates may include: linearly translating the plural left ventricle boundary coordinates; rotating the linearly translated plural left ventricle boundary coordinates in the same plane; and rotating the rotated plural left ventricle boundary coordinates in a space.

In linearly translating the left ventricle boundary coordinates, the controller may linearly translate the plural left ventricle boundary coordinates such that centers of gravity of the left ventricle boundary coordinates are matched with a predetermined reference point.

In calculating the position of the left ventricle in 3D space through transformation of the left ventricle boundary coordinates, the controller may calculate respective angles at which the plural left ventricle boundary coordinates are rotated in the same plane and in a space using an alternating minimization optimization method.

In accordance with another aspect of the present invention, an apparatus for generating a 3D left ventricle image includes: an ultrasonic sensor transmitting ultrasonic waves to the heart and receiving echoes thereof; an image processor acquiring a 2D left ventricle image based on the echoes of the ultrasonic waves and extracting left ventricle boundary coordinates from the 2D left ventricle image; and a controller calculating a position of the left ventricle in 3D space through transformation of the left ventricle boundary coordinates extracted by the image processor and generating a 3D left ventricle image based on the position of the left ventricle in 3D space.

The ultrasonic sensor may transmit ultrasonic waves to the heart in three different directions and receive echoes of the ultrasonic waves in each direction.

The image processor acquires a plurality of 2D images, wherein the plurality of 2D images comprises a 2-chamber view, a 3-chamber view, and a 4-chamber view for an entire cardiac cycle.

The image processor may extract respective left ventricle boundary coordinates from the plurality of 2D images.

The controller may linearly translate the plural left ventricle boundary coordinates, rotate the linearly translated plural left ventricle boundary coordinates in the same plane, and rotate the rotated plural left ventricle boundary coordinates in a space, thereby calculating the position of the left ventricle in 3D space.

The controller may linearly translate the plural left ventricle boundary coordinates such that centers of gravity of the plural left ventricle boundary coordinates are matched with a predetermined reference point.

The controller may calculate respective angles at which the plural left ventricle boundary coordinates are rotated in the same plane and in a space using an alternating minimization optimization method.

According to the present invention, it is possible to generate and visualize a 3D boundary of a left ventricle of the heart using 2D echocardiograms of the heart.

Further, the present invention has a high commercial worth for use in a clinical test for diagnosis of heart function, since it can provide 3D information on the left ventricle of the heart.

BRIEF DESCRIPTION OF THE DRAWINGS

The above and other aspects, features, and advantages of the present invention will become apparent from the detailed description of the following embodiments in conjunction with the accompanying drawings, in which.

DETAILED DESCRIPTION

Hereinafter, exemplary embodiments of the present invention will be described in detail with reference to the accompanying drawings. It should be noted that the drawings are not to precise scale and may be exaggerated in thickness of lines or size of components for descriptive convenience and clarity only. In addition, the terms used herein are defined by taking functions of the present invention into account and can be changed according to user or operator custom or intention. Therefore, definition of the terms should be made according to the overall disclosure set forth herein.

Figure 1:
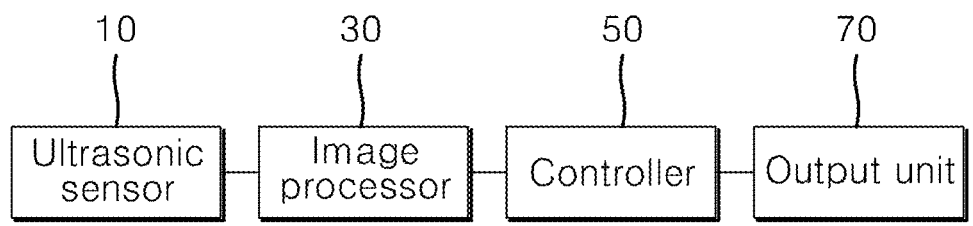
FIG. 1 is a block diagram of an apparatus for generating a 3D left ventricle image according to one embodiment of the present invention.

FIG. 1 is a block diagram of an apparatus for generating a 3D left ventricle image according to one embodiment of the present invention.

Referring to FIG. 1, the apparatus for generating a 3D left ventricle image includes an ultrasonic sensor 10, an image processor 30, a controller 50, and an output unit 70.

The ultrasonic sensor 10 transmits ultrasonic waves to the heart and receives echoes of the ultrasonic waves.

Particularly, in this embodiment, the ultrasonic sensor 10 may transmit ultrasonic waves to the heart in three different directions for the same cardiac cycle and receive echoes thereof in each direction.

The image processor 30 extracts boundary coordinates of a left ventricle of the heart from a 2D image of the left ventricle. Specifically, the image processor acquires a 2D left ventricle image based on the echoes of the ultrasonic waves received by the ultrasonic sensor 10, and extracts left ventricle boundary coordinates from the 2D left ventricle image.

Particularly, in this embodiment, since ultrasonic waves are transmitted to the heart in three different directions from the ultrasonic sensor 10, as described above, the image processor 30 may acquire a plurality of 2D left ventricle images, specifically a 2-chamber view, a 3-chamber view, and a 4-chamber view, based on echoes of the ultrasonic waves in each direction.

In other words, the image processor 30 may acquire 2D sectional images of the heart captured from three different directions for the same cardiac cycle, and extract respective left ventricle boundary coordinates from the acquired plural images.

Here, each of the 2D images acquired by the image processor 30 may be an apical view, which refers to an image obtained by capturing an internal section of the heart along a long axis of the heart.

As such, in this embodiment, apical views captured from three different directions are taken to generate a 3D image of the heart based on echocardiograms.

Figure 2:
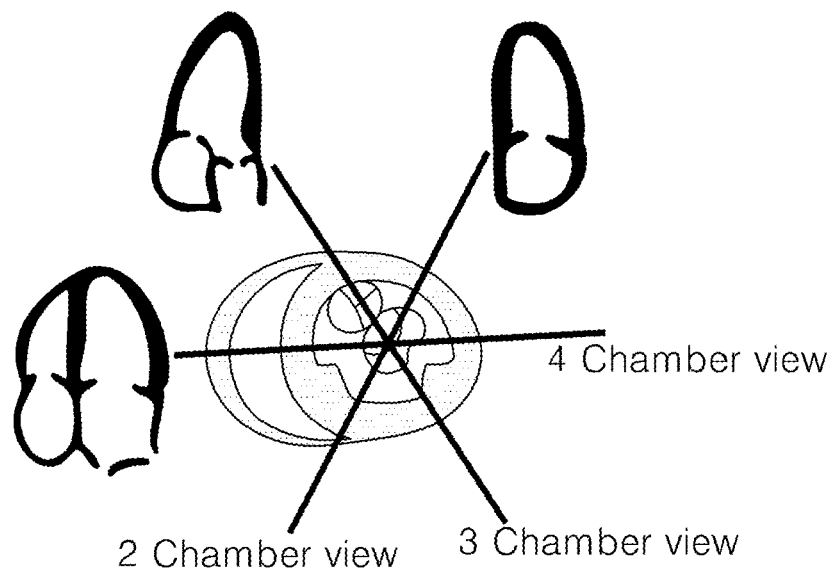
FIG. 2 is a view showing 2D images which can be acquired based on received signals corresponding to ultrasonic waves transmitted to the heart in three different directions.

FIG. 2 is a view showing 2D images which can be obtained based on received signals corresponding to ultrasonic waves transmitted to the heart in three different directions.

Referring to FIG. 2, based on received echoes corresponding to ultrasonic waves transmitted to the heart in three different directions, it is possible to acquire a 2-chamber view, a 3-chamber view, and a 4-chamber view, from each of which left ventricle boundary coordinates may, in turn, be extracted.

Since anatomical boundary data for all ventricles of the heart can be obtained when echocardiograms are captured from three different directions in the above-described manner, a 3D left ventricle image can be generated based on the three echocardiograms.

The controller 50 calculates a position of the left ventricle in 3D space through transformation of the left ventricle boundary coordinates extracted by the image processor 30, and generates a 3D left ventricle image based on the calculated position.

Specifically, in order to calculate the position of the left ventricle in 3D space through transformation of the left ventricle boundary coordinates, first, the controller 50 linearly translates each of the plural left ventricle boundary coordinates extracted by the image processor 30.

Here, the controller 50 linearly translates the plural left ventricle boundary coordinates such that centers of gravity of the plural left ventricle boundary coordinates are matched with a predetermined reference point.

In other words, in this embodiment, since each of the 2-chamber, 3-chamber, and 4-chamber views is to be rotated to generate a 3D image of the entire left ventricle, the controller 50 matches the centers of gravity of the 2D images with one another to transform the boundary coordinates on each 2D image with respect to the same position to generate the 3D image.

Next, the controller 50 rotates the linearly translated plural left ventricle boundary coordinates in the same plane, and then rotates the rotated plural left ventricle boundary coordinates in a space, thereby generating a 3D image of the left ventricle based on each of the boundary coordinates of the left ventricle.

Figure 3:
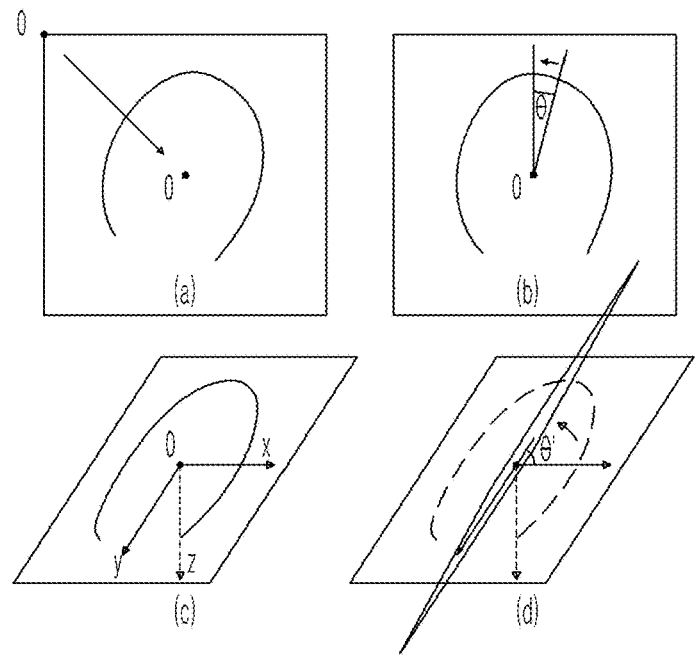
FIG. 3 is a view showing a process of coordinate transformation for calculating a position of the left ventricle in 3D space according to transformation of boundary coordinates extracted from the 2D images.

FIG. 3 is a view showing a process of coordinate transformation for calculating a position of the left ventricle in 3D space through transformation of the boundary coordinates extracted from the 2D images.

Referring to FIG. 3, in the process of calculating the position of the left ventricle in 3D space through transformation of the boundary coordinates extracted from the 2D images, the controller 50 linearly translates the left ventricle boundary coordinates, as shown in FIG. 3(a), rotates the linearly translated left ventricle boundary coordinates in the same plane, as shown in FIG. 3(b), and rotates the rotated left ventricle boundary coordinates in a space, as shown in FIG. 3(c) and FIG. 3(d), thereby generating a 3D image of the left ventricle.

Specifically, assuming that coordinates obtained by linearly translating the boundary coordinates on the 2-chamber view are $(x_{o2}, y_{o2})$, an angle at which the boundary coordinates are rotated in the same plane is $\theta_2$, and an angle at which the boundary coordinates are rotated in a space is $\varphi_2$, a relationship of the left ventricle boundary coordinates in 3D space after completion of rotation with the left ventricle boundary coordinates in a 2D plane before rotation is given by Equation 1:

$$\begin{bmatrix} X_{i2} \\ Y_{i2} \\ Z_{i2} \end{bmatrix} = \begin{bmatrix} \cos\phi_2 & 0 & \sin\phi_2 \\ 0 & 1 & 0 \\ -\sin\phi_2 & 0 & \cos\phi_2 \end{bmatrix} \begin{bmatrix} \cos\theta_2 & -\sin\theta_2 \\ \sin\theta_2 & \cos\theta_2 \\ 0 & 0 \end{bmatrix} \begin{bmatrix} x_{i2} - x_{02} \\ y_{i2} - y_{02} \end{bmatrix}$$

$$= \begin{bmatrix} \cos\phi_2\cos\theta_2 & -\cos\phi_2\sin\theta_2 \\ \sin\theta_2 & \cos\theta_2 \\ -\sin\phi_2\cos\theta_2 & \sin\phi_2\sin\theta_2 \end{bmatrix} \begin{bmatrix} x_{i2} - x_{02} \\ y_{i2} - y_{02} \end{bmatrix}$$

(where $X_{i2}$, $y_{i2}$, and $Z_{i2}$ denote the $i^{th}$ boundary coordinates of the left ventricle in 3D space generated through transformation of the boundary coordinates of the 2-chamber view).

In addition, assuming that coordinates obtained by linearly translating the boundary coordinates on the 3-chamber view, an angle at which the boundary coordinates are rotated in the same plane, and an angle at which the boundary coordinates are rotated in a space are $(x_{o3}, y_{o3})$, $\theta_3$, and $\varphi_3$, respectively, and coordinates obtained by linearly translating the boundary coordinates on the 4-chamber view, an angle at which the boundary coordinates are rotated in the same plane, and an angle at which the boundary coordinates are rotated in a space are $(x_{o4}, y_{o4})$, $\theta_4$, and $\varphi_4$, respectively, relationships of the boundary coordinates of the left ventricle in 3D space with the left ventricle boundary coordinates in a 2D plane before rotation are given by Equations 2 and 3, respectively:

$$\begin{bmatrix} X_{i3} \\ Y_{i3} \\ Z_{i3} \end{bmatrix} = \begin{bmatrix} \cos\phi_3 & 0 & \sin\phi_3 \\ 0 & 1 & 0 \\ -\sin\phi_3 & 0 & \cos\phi_3 \end{bmatrix} \begin{bmatrix} \cos\theta_3 & -\sin\theta_3 \\ \sin\theta_3 & \cos\theta_3 \\ 0 & 0 \end{bmatrix} \begin{bmatrix} x_{i3} - x_{03} \\ y_{i3} - y_{03} \end{bmatrix} \quad \text{[Equation 2]}$$

$$= \begin{bmatrix} \cos\phi_3\cos\theta_3 & -\cos\phi_3\sin\theta_3 \\ \sin\theta_3 & \cos\theta_3 \\ -\sin\phi_3\cos\theta_3 & \sin\phi_3\sin\theta_3 \end{bmatrix}$$

$$\begin{bmatrix} X_{i4} \\ Y_{i4} \\ Z_{i4} \end{bmatrix} = \begin{bmatrix} \cos\phi_4 & 0 & \sin\phi_4 \\ 0 & 1 & 0 \\ -\sin\phi_4 & 0 & \cos\phi_4 \end{bmatrix} \begin{bmatrix} \cos\theta_4 & -\sin\theta_4 \\ \sin\theta_4 & \cos\theta_4 \\ 0 & 0 \end{bmatrix} \begin{bmatrix} x_{i4} - x_{04} \\ y_{i4} - y_{04} \end{bmatrix} \quad \text{[Equation 3]}$$

$$= \begin{bmatrix} \cos\phi_4\cos\theta_4 & -\cos\phi_4\sin\theta_4 \\ \sin\theta_4 & \cos\theta_4 \\ -\sin\phi_4\cos\theta_4 & \sin\phi_4\sin\theta_4 \end{bmatrix}$$

In this embodiment, since a 3D image of the left ventricle is to be generated through transformation of the boundary coordinates on the 2D images, when knowing variable values of degrees by which the boundary coordinates of the 2-chamber, 3-chamber, and 4-chamber views as shown in Equations 1, 2 and 3 are linearly translated, rotated in the same plane, and rotated in a space, it is possible to predict how the 3D left ventricle image will be generated.

Further, assuming that $$\begin{bmatrix} \cos\phi_2\cos\theta_2 & -\cos\phi_2\sin\theta_2 \\ \sin\theta_2 & \cos\theta_2 \\ -\sin\phi_2\cos\theta_2 & \sin\phi_2\sin\theta_2 \end{bmatrix}$$

in Equation 1 is a matrix $A_2$, since $A_2^T A_2 = I$ (Identity matrix), Equation 1 can be arranged as Equation 4:

$$\begin{bmatrix} x_{i2} - x_{02} \\ y_{i2} - y_{02} \end{bmatrix} = \begin{bmatrix} \cos\phi_2\cos\theta_2 & \sin\theta_2 & -\sin\phi_2\cos\theta_2 \\ -\cos\phi_2\sin\theta_2 & \cos\theta_2 & \sin\phi_2\sin\theta_2 \end{bmatrix} \begin{bmatrix} X_{i2} \\ Y_{i2} \\ Z_{i2} \end{bmatrix}$$

Here, since $(x_{o2}, y_{o2})$ can be calculated based on coordinate positions of the reference point and the centers of gravity of the left ventricle boundary coordinates on the 2D image, and $(x_{i2}, y_{i2})$ are the left ventricle boundary coordinates on the 2D image extracted by the image processor 30, $(x_{i2}-x_{o2}, y_{i2}-y_{o2})$ are calculated as a constant value.

Similarly, Equations 2 and 3 with respect to the 3-chamber and 4-chamber views can be arranged as Equations 5 and 6, respectively.

$$\begin{bmatrix} x_{i3} - x_{03} \\ y_{i3} - y_{03} \end{bmatrix} = \begin{bmatrix} \cos\phi_3\cos\theta_3 & \sin\theta_3 & -\sin\phi_3\cos\theta_3 \\ -\cos\phi_3\sin\theta_3 & \cos\theta_3 & \sin\phi_3\sin\theta_3 \end{bmatrix} \begin{bmatrix} X_{i3} \\ Y_{i3} \\ Z_{i3} \end{bmatrix} \quad \text{[Equation 5]}$$

$$\begin{bmatrix} x_{i4} - x_{04} \\ y_{i4} - y_{04} \end{bmatrix} = \begin{bmatrix} \cos\phi_4\cos\theta_4 & \sin\theta_4 & -\sin\phi_4\cos\theta_4 \\ -\cos\phi_4\sin\theta_4 & \cos\theta_4 & \sin\phi_4\sin\theta_4 \end{bmatrix} \begin{bmatrix} X_{i4} \\ Y_{i4} \\ Z_{i4} \end{bmatrix} \quad \text{[Equation 6]}$$

Equations 4, 5, and 6 are linear equations in the form of AX=b, and the relationship of a vector obtained by combining the left ventricle boundary coordinates extracted from the images captured from the three different directions with a corresponding vector in 3D space can be considered as a problem of finding the coefficients of the matrix A and the vector X for b, which is measurable based on Equation 7:

$$b = \begin{bmatrix} \begin{bmatrix} A_2 & & 0 \\ & \ddots & \\ 0 & & A_2 \end{bmatrix} & & \\ & \begin{bmatrix} A_3 & & 0 \\ & \ddots & \\ 0 & & A_3 \end{bmatrix} & \\ & & \begin{bmatrix} A_4 & & 0 \\ & \ddots & \\ 0 & & A_4 \end{bmatrix} \end{bmatrix} X$$

where the left-hand side is a vector obtained by combining vectors of n boundary coordinates extracted from the three images and having (3*n*2) columns and 1 row; X in the right-hand side is a vector obtained by combining position vectors in 3D space corresponding to the left-hand side and having (3*n*3) columns and 1 row; and $A_2$, $A_3$, and $A_4$ denote matrices representing linear transformation in Equations 4, 5, and 6, respectively.

In other words, assuming that a matrix composed of $A_2$, $A_3$, and $A_4$ and multiplying the vector X in the right-hand side is A, by finding the coefficients of the matrix A, it is possible to know by what degrees the boundary coordinates on the 2D 2-chamber, 3-chamber and 4-chamber views are to be rotated in the same plane and in a space in order to obtain the 3D image to be generated, and by finding the vector X, it is possible to figure out the boundary coordinates of the 3D image.

Thus, in this embodiment, the matrix A and the vector X are sequentially found from Equation 7 using an alternating minimization method. However, it is understood that the solution of Equation 7 can be found not only by the aforementioned method but also using various methods in the art.

The alternating minimization method is a method wherein, in calculation of multiple parameters, calculating the optimal solution for one parameter with other parameters fixed is repeatedly conducted for each of the multiple parameters, thereby calculating optimal solutions for all of the multiple parameters to satisfy any given specific conditions.

Since alternating minimization is well known in the art, descriptions of specific calculation processes thereof will be omitted.

Figure 4:
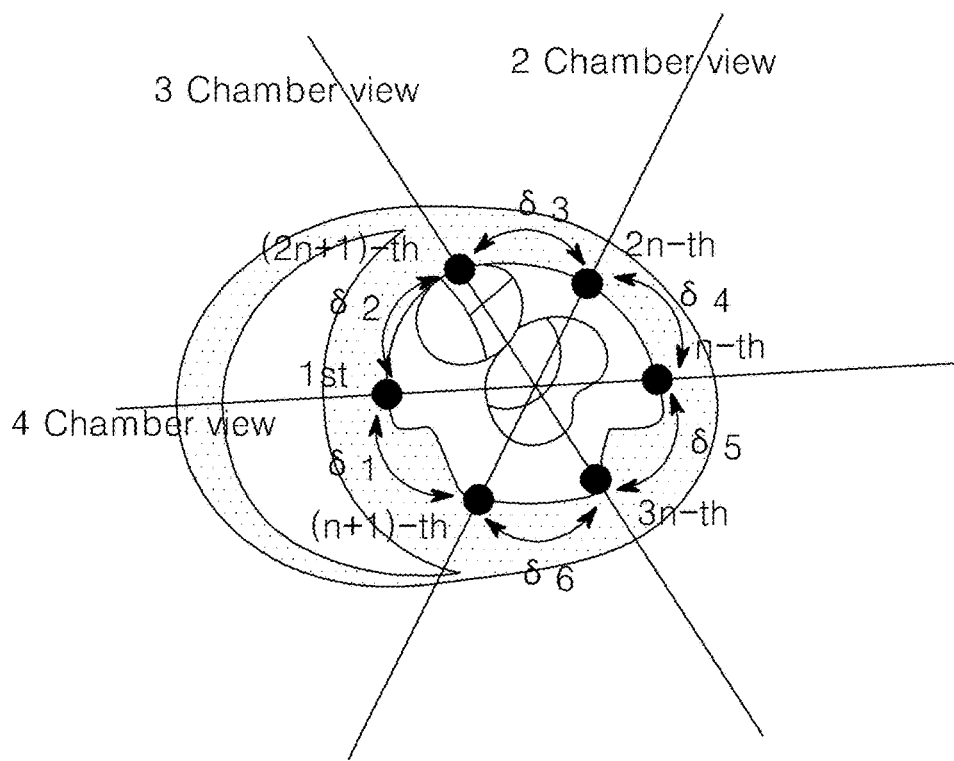
FIG. 4 is a view showing 6 coordinates formed by intersection of the mitral annulus with the boundary coordinates on the 2D images taken from the three different directions, and distances between the adjacent coordinates.

FIG. 4 is a view showing 6 boundary coordinates formed by intersection of the mitral annulus with the boundary coordinates on the 2D images taken from the three different directions, and distances between the adjacent coordinates.

Reviewing conditions for calculation of Equation 7 with reference to FIG. 4, n boundary coordinates of the left ventricle are set to be extracted from each 2D image.

Accordingly, the 1st to $n^{th}$ left ventricle boundary coordinates, the $n+1^{th}$ to $2n^{th}$ left ventricle boundary coordinates, and the $2n+1^{th}$ to $3n^{th}$ left ventricle boundary coordinates are sequentially extracted from the 4-chamber view, the 2-chamber view, and the 3-chamber view, respectively.

Here, each of the boundary coordinates represents a position in 3D space, and thus has an x-axis value, a y-axis value, and a z-axis value. When these x-axis, y-axis, and z-axis values are arranged in order, 3n axis values are obtained for each chamber view, since n boundary coordinates are set to be extracted from each chamber view.

Thus, the 1st to $3n^{th}$ x-axis, y-axis, and z-axis values of the left ventricle, the $3n^{th}$ to $6n^{th}$ x-axis, y-axis, and z-axis values of the left ventricle, and the $6n+1^{th}$ to $9n^{th}$ x-axis, y-axis, and z-axis values of the left ventricle are sequentially extracted from the 4-chamber view, the 2-chamber view, and the 3-chamber view, respectively.

Specifically, the boundary coordinates extracted from the 4-chamber view are $(x_{(1)}, x_{(2)}, x_{(3)})$ and $(x_{(3n-2)}, x_{(3n-1)}, x_{(3n)})$.

Further, the boundary coordinates extracted from the 2-chamber view are $(x_{(3n+1)}, x_{(3n+2)}, x_{(3n+3)})$ and $(x_{(6n-2)}, x_{(6n-1)}, x_{(6n)})$, and the boundary coordinates extracted from the 3-chamber view are $(x_{(6n+1)}, x_{(6n+2)}, x_{(6n+3)})$ and $(x_{(9n-2)}, x_{(9n-1)}, x_{(9n)})$.

Thus, the distances between the boundary coordinates may be represented by Equation 8:

$$q_1(x)(:=(x_{(1)}-x_{(3n+1)})^2+(x_{(2)}-x_{(3n+2)})^2+(x_{(3)}-x_{(3n+3)})^2)=\delta_1^2$$

$$q_2(x)(:=(x_{(1)}-x_{(6n+1)})^2+(x_{(2)}-x_{(6n+2)})^2+(x_{(3)}-x_{(6n+3)})^2)=\delta_2^2$$

$$q_3(x)(:=(x_{(6n+1)}-x_{(6n-2)})^2+(x_{(6n+2)}-x_{(6n-1)})^2+(x_{(6n+3)}-x_{(6n)})^2)=\delta_3^2$$

$$q_4(x)(:=(x_{(6n-2)}-x_{(3n-2)})^2+(x_{(6n-1)}-x_{(3n-1)})^2+(x_{(6n)}-x_{(3n)})^2)=\delta_4^2$$

$$q_5(x)(:=(x_{(3n-2)}-x_{(9n-2)})^2+(x_{(3n-1)}-x_{(9n-1)})^2+(x_{(3n)}-x_{(9n)})^2)=\delta_5^2$$

$$q_6(x)(:=(x_{(9n-2)}-x_{(3n+1)})^2+(x_{(9n-1)}-x_{(3n+2)})^2+(x_{(9n)}-x_{(3n+3)})^2)=\delta_6^2$$

where $q_i(x)$ is a quadratic function expressed by the square of distances between adjacent coordinates of 6 boundary coordinates at the mitral annulus, and $\delta_i(>0)$ can be given as ½ of the maximum value of distance between each two points at the mitral annulus on each view.

Hereinafter, to find the solution of AX=b, Equation 7 will be transformed into Equation 9 based on Equation 8 which represents a precondition that expansion or contraction of the left ventricle does not cause changes in the total length of the mitral annulus.

$$\min\{\|Ax-b\|_2^2: AA^T=I, q_i(x)\leq\delta_i^2, \text{ for } i=1,\ldots,6\} \quad \text{[Equation 9]}$$

Further, assuming $A^T=B$, Equation 9 may be expressed by Equation 10.

$$\min\{\|Ax-b\|_2^2: B^TB=I, A^T=B, q_i(x)\leq\delta_i^2, \text{ for } i=1,\ldots,6\} \quad \text{[Equation 10]}$$

In addition, Equation 10 may be transformed into Equation 11.

$$\min\{\|Ax-b\|_2^2 + \frac{\alpha}{2}\|A^T-B\|_F^2 : B^TB=I, \quad \text{[Equation 11]}$$
$$q_i(x)\leq\delta_i^2, \text{ for } i=1,\ldots,6\}$$

(where $\alpha$ has a positive value which may be determined by experimentation, and $\|\cdot\|_F$ denotes a Frobenius norm of the matrix.)

Since, to calculate Equation 11, respective optimal solutions for A, B and X must be found, A, B and X may be calculated using a three-level alternating method such as Equation 12:

$$x^{k+1} = \operatorname{argmin}_x \{\|A^k x - b\|_2^2 : q_i(x) \leq \delta_i^2\}$$

$$A^{k+1} = \operatorname{argmin}_A \{\|A x^{k+1} - b\|_2^2 + \alpha/2 \|A^T - B^k\|_F^2\}$$

$$B^{k+1} = \operatorname{argmin} \{\|(A^{k+1})^T - B\|_F^2 : B^T B = I\}$$

In this embodiment, to calculate X, A, and B, a three-block nonlinear Gauss-Seidal method using a quadratically constrained quadratic program (QCQP) and a feasible method were employed.

However, it should be understood that the present invention is not limited thereto, and the optimal solutions for A, B, X can thus be calculated using other suitable calculation methods. Equation 9 can be expressed by Equation 13 for B, where $B = A^T$, instead of Equations 10 and 11.

$$\min_{B,x} \{\|B^T x - b\|_2^2 : B^T B = I, q_i(x) \leq \delta^2\} \quad \text{[Equation 13]}$$

In this embodiment, to calculate X and B in Equation 13, a two-block nonlinear Gauss-Seidal method using a quadratically constrained quadratic program (QCQP) and a feasible method may also be employed.

Briefly reviewing a process of calculating each variable using the aforementioned optimization method, the given problem may be represented by Equation 14 in order to use the QCQP.

$$\min_x = x^T A^T A x - 2 b^T (A x),$$

$$q_i(x)(:= x^T P_i x) - \delta^2 \leq 0, \, i = 1, \ldots, 6 \quad \text{[Equation 14]}$$

Further, the matrix $P_i$ in Equation 14 is determined by Equations 15 to 20.

$$P_1 = \begin{bmatrix} \begin{bmatrix} I_{3\times3} & 0 & 0 \\ 0 & \ddots & \vdots \\ 0 & \cdots & 0 \end{bmatrix} & \begin{bmatrix} -I_{3\times3} & 0 & 0 \\ 0 & \ddots & \vdots \\ 0 & \cdots & 0 \end{bmatrix} \\ \begin{bmatrix} -I_{3\times3} & 0 & 0 \\ 0 & \ddots & \vdots \\ 0 & \cdots & 0 \end{bmatrix} & \begin{bmatrix} I_{3\times3} & 0 & 0 \\ 0 & \ddots & \vdots \\ 0 & \cdots & 0 \end{bmatrix} \\ & \begin{bmatrix} 0 & & 0 \\ & \ddots & \\ 0 & & 0 \end{bmatrix} \end{bmatrix} \quad \text{[Equation 15]}$$

$$P_2 = \begin{bmatrix} \begin{bmatrix} I_{3\times3} & 0 & 0 \\ 0 & \ddots & \vdots \\ 0 & \cdots & 0 \end{bmatrix} & \begin{bmatrix} -I_{3\times3} & 0 & 0 \\ 0 & \ddots & \vdots \\ 0 & \cdots & 0 \end{bmatrix} \\ & \begin{bmatrix} 0 & & 0 \\ & \ddots & \\ 0 & & 0 \end{bmatrix} \\ \begin{bmatrix} -I_{3\times3} & 0 & 0 \\ 0 & \ddots & \vdots \\ 0 & \cdots & 0 \end{bmatrix} & \begin{bmatrix} I_{3\times3} & 0 & 0 \\ 0 & \ddots & \vdots \\ 0 & \cdots & 0 \end{bmatrix} \end{bmatrix} \quad \text{[Equation 16]}$$

$$P_3 = \begin{bmatrix} \begin{bmatrix} 0 & & 0 \\ & \ddots & \\ 0 & & 0 \end{bmatrix} \\ & \begin{bmatrix} 0 & \cdots & 0 \\ \vdots & \ddots & 0 \\ 0 & 0 & I_{3\times3} \end{bmatrix} & \begin{bmatrix} 0 & \cdots & 0 \\ 0 & \ddots & 0 \\ -I_{3\times3} & 0 & 0 \end{bmatrix} \\ & \begin{bmatrix} 0 & 0 & -I_{3\times3} \\ \vdots & \ddots & 0 \\ 0 & \cdots & 0 \end{bmatrix} & \begin{bmatrix} I_{3\times3} & 0 & 0 \\ 0 & \ddots & \vdots \\ 0 & \cdots & 0 \end{bmatrix} \end{bmatrix} \quad \text{[Equation 17]}$$

$$P_4 = \begin{bmatrix} \begin{bmatrix} 0 & \cdots & 0 \\ \vdots & \ddots & 0 \\ 0 & 0 & I_{3\times3} \end{bmatrix} & \begin{bmatrix} 0 & \cdots & 0 \\ \vdots & \ddots & 0 \\ 0 & 0 & -I_{3\times3} \end{bmatrix} \\ \begin{bmatrix} 0 & \cdots & 0 \\ \vdots & \ddots & 0 \\ 0 & 0 & -I_{3\times3} \end{bmatrix} & \begin{bmatrix} 0 & \cdots & 0 \\ \vdots & \ddots & 0 \\ 0 & 0 & I_{3\times3} \end{bmatrix} \\ & \begin{bmatrix} 0 & & 0 \\ & \ddots & \\ 0 & & 0 \end{bmatrix} \end{bmatrix} \quad \text{[Equation 18]}$$

$$P_5 = \begin{bmatrix} \begin{bmatrix} 0 & \cdots & 0 \\ \vdots & \ddots & 0 \\ 0 & 0 & I_{3\times3} \end{bmatrix} & \begin{bmatrix} 0 & \cdots & 0 \\ \vdots & \ddots & 0 \\ 0 & 0 & -I_{3\times3} \end{bmatrix} \\ & \begin{bmatrix} 0 & & 0 \\ & \ddots & \\ 0 & & 0 \end{bmatrix} \\ \begin{bmatrix} 0 & \cdots & 0 \\ \vdots & \ddots & 0 \\ 0 & 0 & -I_{3\times3} \end{bmatrix} & \begin{bmatrix} 0 & \cdots & 0 \\ \vdots & \ddots & 0 \\ 0 & 0 & I_{3\times3} \end{bmatrix} \end{bmatrix} \quad \text{[Equation 19]}$$

$$P_6 = \begin{bmatrix} \begin{bmatrix} 0 & & 0 \\ & \ddots & \\ 0 & & 0 \end{bmatrix} \\ & \begin{bmatrix} I_{3\times3} & 0 & 0 \\ 0 & \ddots & \vdots \\ 0 & \cdots & 0 \end{bmatrix} & \begin{bmatrix} 0 & 0 & -I_{3\times3} \\ \vdots & \ddots & 0 \\ 0 & \cdots & 0 \end{bmatrix} \\ \begin{bmatrix} 0 & \cdots & 0 \\ 0 & \ddots & \vdots \\ -I_{3\times3} & 0 & 0 \end{bmatrix} & \begin{bmatrix} 0 & \cdots & 0 \\ \vdots & \ddots & 0 \\ 0 & 0 & I_{3\times3} \end{bmatrix} \end{bmatrix} \quad \text{[Equation 20]}$$

Since specific processes of calculating X using the aforementioned matrix and Equation 14 are well known in the art, descriptions thereof will be omitted.

Further, A may be calculated based on Equation 21:

$$A^{(k+1)} = (B^{(k)} + b(x^{(k+1)})^T)(x^{(k+1)}(x^{(k+1)})^T + \alpha I)^{-1}$$

Based on the aforementioned optimization method, the controller 50 may calculate: the coordinates to which the 2D 2-chamber, 3-chamber, 4-chamber views are linearly translated; $\theta_2$, $\theta_3$, and $\theta_4$, the respective angles at which of the 2D 2-chamber, 3-chamber, 4-chamber views are rotated in the same plane; and $\varphi_2$, $\varphi_3$, and $\varphi_4$, the respective angles at which of the 2D 2-chamber, 3-chamber, 4-chamber views are rotated in a space.

As such, since the controller 50 can calculate all of the respective rotation angles of the 2-chamber, 3-chamber, 4-chamber views, it is possible to obtain the respective rotation angles of the chamber views needed to generate a 3D image of the left ventricle using the chamber views.

In other words, based on $\theta_2$, $\theta 3$, and $\theta_4$, it is possible to know by what degree each of the chamber views is rotated in a space to allow the left ventricle boundary to be generated in the 3D image of the entire left ventricle.

As such, the controller 50 generates one 3D model based on the 2-chamber, 3-chamber, 4-chamber views extracted for the same cardiac cycle, and thus can generate the left ventricle boundary coordinates in the 3D image of the entire left ventricle. Particularly, in this embodiment, the 2-chamber, 3-chamber, 4-chamber views are acquired for the entire cardiac cycle, whereby it is possible to know a 3D motion of the left ventricle during the entire cardiac cycle.

Further, to generate a 3D image by the aforementioned process, the boundary coordinates before and after rotation of the plural 2D images in a space must be connected to each other.

Thus, in this embodiment, the controller 50 may generate a 3D image of the left ventricle of the heart using a level set method based on three apical views.

In the level set method, the term "zero level set" means a surface composed of a set of vectors for which a level set function has a value of 0, and the level set function has a positive value inside a region surrounded by the zero level set and a negative value outside the region, with a vector, indicating a position, as a factor.

Thus, the 3D image of the left ventricle of the heart may be generated by numerically calculating the zero level set. For example, to include left ventricle boundary data of a surface for which a zero level set is measured, energy of a level set is given by Equation 22:

$$E(\Gamma)=E(\phi)=[\int d^P(x)\delta(\phi(x))|\nabla\phi(x)|dx]^{1/p}$$

where $\Gamma$ denotes a zero level set, $\phi$ denotes a level set function, x denotes a position vector, $\delta(x)$ denotes a one dimensional delta function, and $\delta(\phi(x))|\nabla\phi(x)|dx$ denotes a surface element in a zero level set of $\phi$.

As such, in this embodiment, for each step of the cardiac cycle, a 3D model of the left ventricle may be constructed using surface energy obtained from the echocardiograms.

Further, as described above, in this embodiment, since the ultrasonic sensor 10 transmits ultrasonic waves to the heart and receives echoes thereof for the same cardiac cycle, the controller 50 may automatically generate a 3D motion of the heart during one cycle for which the heart contracts and expands The output unit 70 allows a user to see a motion, such as contraction or expansion of the heart by outputting the 3D image of the left ventricle generated by the controller 50.

Although the above embodiment has been described by way of example wherein the 3D image of the left ventricle is automatically generated using the 2D echocardiograms of the heart, the present invention is not limited thereto. Thus, a 3D image of the entire heart may also be generated.

Figure 5:
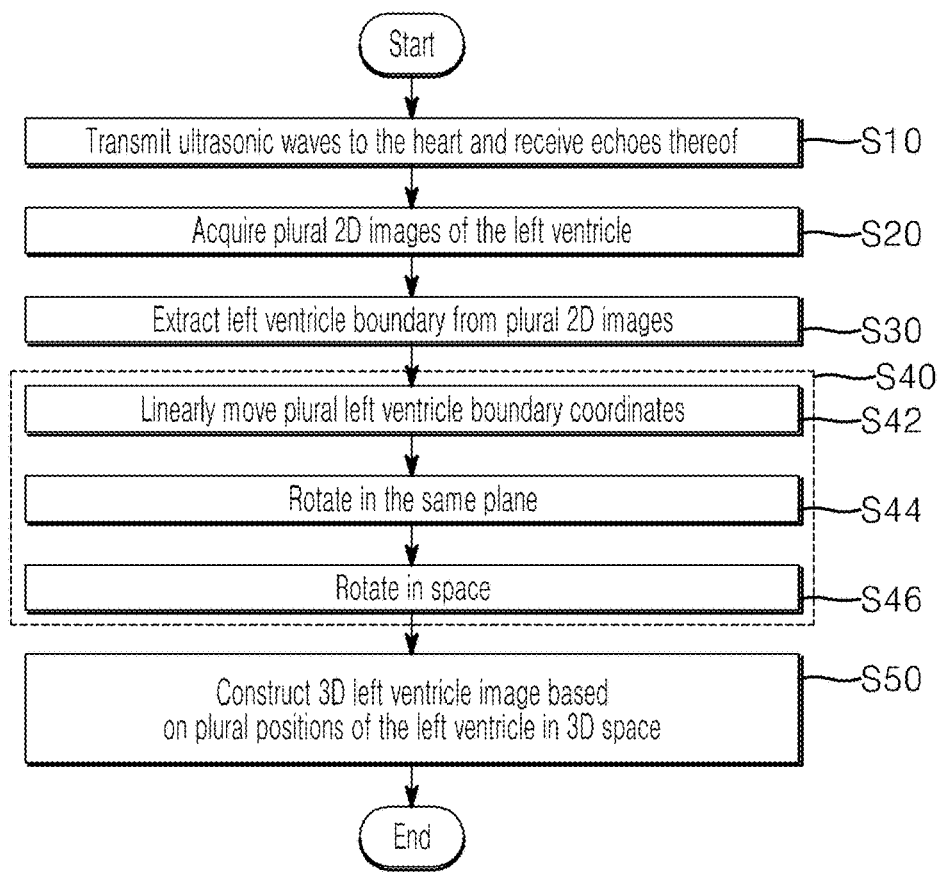
FIG. 5 is a flowchart of a method for generating a 3D left ventricle image according to one embodiment of the present invention.

FIG. 5 is a flowchart of a method for generating a 3D left ventricle image according to one embodiment of the present invention.

Referring to FIG. 5, in the method for generating a 3D left ventricle image according to the embodiment, first, the ultrasonic sensor 10 transmits ultrasonic waves to the heart and receives echoes of the ultrasonic waves (S10).

Particularly, in this embodiment, the ultrasonic sensor 10 may transmit ultrasonic waves to the heart in three different directions for the same cardiac cycle and receive echoes thereof in each direction.

The image processor 30 acquires a 2D image of the left ventricle based on the echoes of the ultrasonic waves (S20), and extracts left ventricle boundary coordinates from the acquired 2D image (S30).

Particularly, since the ultrasonic sensor 10 transmits ultrasonic waves to the heart in three different directions, the image processor 30 may acquire a plurality of 2D images of the left ventricle, specifically a 2-chamber view, a 3-chamber view, and a 4-chamber view, based on echoes of the ultrasonic waves in each direction.

In other words, the image processor 30 may acquire 2D sectional images captured from three different directions for the same cardiac cycle, and extract respective left ventricle boundary coordinates from the acquired plural images.

Next, the controller 50 calculates a position of the left ventricle in 3D space through transformation of the left ventricle boundary coordinates extracted by the image processor 30 (S40).

Specifically, in the aforementioned step (S40), first, the controller 50 linearly translates each of the plural left ventricle boundary coordinates extracted by the image processor 30 (S42).

Here, the controller 50 linearly translates the plural left ventricle boundary coordinates such that centers of gravity of the plural left ventricle boundary coordinates are matched with a predetermined reference point.

In other words, in this embodiment, since a 3D image of the entire left ventricle is to be constructed by rotating the respective left ventricle boundary coordinates on the 2-chamber, 3-chamber, and 4-chamber views, the controller 50 matches the centers of gravity of the respective left ventricle boundary coordinates on the 2D images with one another to transform the boundary coordinates of each 2D image with respect to the same position to generate a 3D image.

Next, the controller 50 rotates the linearly translated plural left ventricle boundary coordinates in the same plane (S44) and then rotates the rotated plural left ventricle boundary coordinates in a space (S46), thereby generating left ventricle boundary coordinates on a 3D image of the left ventricle based on the respective left ventricle boundary coordinates on the 2D images.

In other words, in this embodiment, the 3D image of the entire left ventricle is generated by rotating each of the plural left ventricle boundary coordinates acquired by transmission of ultrasonic waves to the heart in three different directions.

Here, an alternating minimization method is used to determine by what degree the respective left ventricle boundary coordinates on the 2D images need to be rotated and to generate the left ventricle boundary coordinates in 3D space.

The alternating minimization method for the given problem includes applying a three-block or two-block nonlinear Gauss-Seidal method using a quadratically constrained quadratic program (QCQP) and a feasible method.

Next, the controller 50 generates a 3D image of the left ventricle based on the plural positions of the left ventricle in 3D space calculated in the aforementioned step (S40), and outputs the 3D image via the output unit 70 to make the left ventricle inside the human body visible from outside.

According to this embodiment, it is possible to generate and visualize a 3D left ventricle boundary using 2D echocardiograms of the heart.

Further, this embodiment has high commercial value for use in a clinical test for diagnosis of heart function, since it can provide 3D information on the left ventricle.

Although the present invention has been described with reference to some embodiments in conjunction with the drawings, it should be understood that these embodiments are provided for illustration only and that various modifications and other equivalent embodiments can be made without departing from the spirit and the scope of the present invention. Thus, the technical scope of the present invention should be determined by the attached claims.

LEGEND OF REFERENCE NUMERALS

10: Ultrasonic sensor
30: Image processor
50: Controller
70: Output unit

What is claimed is:

1. A method for generating a 3D image of a left ventricle of the heart, comprising:

acquiring, by an image processor, a plurality of 2D left ventricle images;

extracting, by the image processor, sets of left ventricle boundary coordinates from the plurality of 2D images, respectively;

before extracting the left ventricle boundary coordinates, transmitting, by an ultrasonic sensor, ultrasonic waves to the heart and receiving echoes thereof, wherein the image processor acquires the plurality of 2D left ventricle images based on the echoes of the ultrasonic waves;

calculating, by a controller, a position of the left ventricle in 3D space through transformation of the extracted sets of left ventricle boundary coordinates;

and generating, by the controller, a 3D left ventricle image based on the calculated position of the left ventricle in 3D space, wherein calculating the position of the left ventricle in 3D space through transformation of the extracted sets of left ventricle boundary coordinates comprises: linearly translating each set of left ventricle boundary coordinates such that centers of gravity of each set of the left ventricle boundary coordinates are matched with a predetermined reference point; rotating the linearly translated sets of left ventricle boundary coordinates in the same plane; and rotating the rotated sets of left ventricle boundary coordinates in a space, wherein, in calculating the position of the left ventricle in 3D space through transformation of the left ventricle boundary coordinates, the controller calculates respective angles at which the sets of left ventricle boundary coordinates are rotated in the same plane and in a space using an alternating minimization optimization method in a condition that expansion or contraction of the left ventricle does not cause changes in the circumferential length of the mitral annulus, and wherein, a rotation transformation matrix and a position vector of the boundary coordinates in 3D space are used as parameters of the alternating minimization optimization method.

2. The method according to claim 1, wherein, in receiving the echoes of the ultrasonic waves, the ultrasonic sensor transmits ultrasonic waves to the heart in three different directions and receives echoes thereof in each direction.

3. The method according to claim 2, wherein, the plurality of 2D images comprising a 2-chamber view, a 3-chamber view, and a 4-chamber view for an entire cardiac cycle.

4. An apparatus for generating a 3D left ventricle image, comprising:

an ultrasonic sensor transmitting ultrasonic waves to the heart and receiving echoes thereof;

an image processor acquiring a plurality of 2D left ventricle images based on the echoes of the ultrasonic waves and extracting sets of left ventricle boundary coordinates from the plurality of 2D images, respectively; and a controller calculating a position of the left ventricle in 3D space through transformation of the sets of left ventricle boundary coordinates extracted by the image processor and generating a 3D left ventricle image based on the position of the left ventricle in 3D space, wherein the controller linearly translates each set of left ventricle boundary coordinates such that centers of gravity of each set of the left ventricle boundary coordinates are matched with a predetermined reference point, rotates the linearly translated sets of left ventricle boundary coordinates in the same plane, and rotates the rotated sets of left ventricle boundary coordinates in a space to calculate the position of the left ventricle in 3D space, wherein the controller calculates respective angles at which the sets of left ventricle boundary coordinates are rotated in the same plane and in a space using an alternating minimization optimization method in a condition that expansion or contraction of the left ventricle does not cause changes in the circumferential length of the mitral annulus, and wherein, a rotation transformation matrix and a position vector of the boundary coordinates in 3D space are used as parameters of the alternating minimization optimization method.

5. The apparatus according to claim 4, wherein the ultrasonic sensor transmits ultrasonic waves to the heart in three different directions and receives echoes of the ultrasonic waves in each direction.

6. The apparatus according to claim 5, wherein the plurality of 2D images comprising a 2-chamber view, a 3-chamber view, and a 4-chamber view for an entire cardiac cycle.

* * * * *